United States Patent [19]

Liu

[11] Patent Number: 4,714,771
[45] Date of Patent: Dec. 22, 1987

[54] PROCESS FOR PREPARING HALOGENATED TRIALKYL PHOSPHATE ESTERS

[75] Inventor: Ming-Biann Liu, Midland, Mich.

[73] Assignee: The Dow Chemical Company, Midland, Mich.

[21] Appl. No.: 802,145

[22] Filed: Nov. 27, 1985

[51] Int. Cl.[4] .............................................. C07F 9/09
[52] U.S. Cl. ................................................... 558/102
[58] Field of Search ....................................... 558/102

[56] References Cited

U.S. PATENT DOCUMENTS

| | | | |
|---|---|---|---|
| 1,766,720 | 6/1930 | Nicolai | 558/92 |
| 1,840,335 | 1/1932 | Horst | 558/211 |
| 2,624,750 | 1/1953 | Pechukas | 558/92 |
| 2,870,192 | 1/1959 | Bonstedt | 558/102 |
| 3,324,205 | 6/1957 | Carpenter et al. | 558/91 |
| 3,830,886 | 8/1974 | Davis et al. | 558/188 |
| 4,046,719 | 9/1977 | Stanaback | 558/203 |

FOREIGN PATENT DOCUMENTS 1098637  1/1968  United Kingdom ................ 558/102
1173252 12/1969  United Kingdom .

OTHER PUBLICATIONS

Derwent Abstract of Japanese, 7106865.
Zakharou et al., English Language Transtation from "Aka. Nauk. SSSR, Seriyakhim", No. 11 (1971), pp. 2503–2509.
Jackson et al., "Chem. Abst.", vol. 80, (1973), 97205h.
Kosolapoff, "Organophosphorus Cpds.", 1951, pp. 211–277.

*Primary Examiner*—Anton H. Sutto
*Attorney, Agent, or Firm*—Barbara J. Sutherland

[57] ABSTRACT

A method of producing a halogenated trialkyl phosphate ester which comprises admixing a halogenated hydroxy compound containing a halogen selected from the group consisting of bromine, chlorine, iodine and mixtures thereof, a phosphorus oxyhalide containing a halogen selected from the group consisting of bromine, chlorine, iodine and mixtures thereof, a solvent suitable to dissolve the halogenated hydroxy compound and the phosphorus oxyhalide, said solvent being substantially inert to hydrogen halide, and a catalyst suitable to increase the polarity of the phosphorus oxyhalide, refluxing said admixture sufficiently to form a trialkyl phosphate ester precipitate, and recovering this precipitate.

58 Claims, No Drawings

PROCESS FOR PREPARING HALOGENATED TRIALKYL PHOSPHATE ESTERS

This invention relates to a new process for preparing halogenated trialkyl phosphate esters from halogenated hydroxy compounds.

BACKGROUND OF THE INVENTION

A number of processes for preparing trialkyl phosphates have been known. These methods, as described in G. M. Kosolapoff, *Organophosphorus Compounds*, (John Wiley & Sons, Inc., New York, 1950), include: (1) the reaction of alkyl halides with metal phosphates; (2) the reaction of alcohols or phenols with phosphorus oxychloride in the presence of tertiary bases; (3) the reaction of phosphorus halides with sodium alkoxides or phenoxides; (4) the reaction of phosphorus oxychloride with an excess of an alcohol or phenol; and (5) the ring opening reactions of olefin oxides with phosphorus oxychloride. While each of these methods is efficacious, only the fourth method—the reaction of phosphorus oxychloride with an excess of alcohol or phenol—is commercially practiced due to economic considerations. In attempting to prepare a halogenated trialkyl phosphate, however, this method is generally ineffective because the phosphorus oxychloride will not by itself significantly react with a halogenated alcohol or phenol.

Economical and efficient methods of producing various halogenated compounds, for use as ignition resistant compositions or for use in such compositions, have been sought. The brominated compounds are known to be particularly useful in promoting ignition resistance. However, because of the bromine content these compounds tend to be unstable to ultraviolet and visible light. This tendency results in color changes, notably yellowing, that harm the cosmetic appearance of the final product into which the ignition resistance compound is incorporated and therefore decrease its commercial desirability. Compounds containing other halogens have similar tendencies.

The halogenated trialkyl phosphates, however, are known to impart ignition resistance while at the same time remain relatively stable to ultraviolet and visible light. Thus, when used in composition with a polymer, a reduced amount of discoloration will occur over time. At least one of these compounds, tris(tribromoneopentyl) phosphate, also acts as a plasticizer, thereby expediting processing when it is used in a composition of varying type. However, methods of preparing this compound and other halogenated trialkyl phosphates have, in the past, been expensive or time consuming, generally attaining only low conversion rates.

Thus, what is needed in the art is a process that is a simple, fast and high yield way to prepare halogenated trialkyl phosphate esters. This disclosure describes such an invention.

SUMMARY OF THE INVENTION

According to the present invention, there is provided a method of producing a halogenated trialkyl phosphate ester which comprises admixing a halogenated hydroxy compound containing a halogen selected from the group consisting of Br, Cl, I and mixtures thereof, a phosphorus oxyhalide containing a halogen selected from the group consisting of Br, Cl, I and mixtures thereof, a solvent suitable to dissolve the halogenated hydroxy compound and the phosphorus oxyhalide, the solvent being substantially inert to hydrogen halide, and a catalyst suitable to increase the polarity of the phosphorus oxyhalide, refluxing said admixture sufficiently to form a trialkyl phosphate ester precipitate, and recovering this precipitate.

DESCRIPTION OF THE PREFERRED EMBODIMENTS

The present invention provides a simple, fast, and high yield method for producing halogenated trialkyl phosphate esters by the reaction of a halogenated hydroxy compound and a phosphorus oxyhalide in the presence of a catalyst. The reactants are dissolved in a solvent which is inert to the hydrogen halide formed in reaction.

The hydroxy compound chosen should contain one or more halogens selected from the group consisting of Br, Cl, I and mixtures of these, preferably Br and Cl, and more preferably Br. The proportion of halogenated hydroxy compound to the phosphorus oxyhalide is more preferably about three moles of the hydroxy compound to about one mole of the phosphorus oxyhalide; however, other proportions are also possible, within the range of about ten to about one and about one to about one, and preferably within the range of about four to about one and about two to about one. An excess of either reactant will affect the percent yield of the desired halogenated trialkyl phosphate ester products and may promote the formation of other species. For example, when tribromoneopentyl alcohol is used as the halogenated hydroxy compound and phosphorus oxychloride is used as the phosphorus oxyhalide, a mole ratio of less than three to one results in the presence of two intermediates, tribromoneopentyl dichlorophosphate and bis(tribromoneopentyl) chlorophosphate, in the product solution along with the desired tris(tribromoneopentyl) phosphate. A mole ratio of greater than three here results in unreacted alcohol in the product solution. Other examples of possible halogenated hydroxy compounds include trichloroneopentyl alcohol, chloro-dibromoneopentyl alcohol, bromo-dichloroneopentyl alcohol and related compounds.

The phosphorus oxyhalide may contain bromine, chlorine or iodine, preferably chlorine. Mixtures of at least two compounds selected from the group consisting of phosphorus oxybromide, phosphorus oxychloride and phosphorus oxyiodide are also possible, although not preferred.

The catalyst is believed to operate to increase the polarity of the phosphorus oxyhalide, thereby making the phosphorus more positive and the chloride more negative than under normal conditions. This increased polarity is believed to facilitate the reaction between the phosphorus oxyhalide and the halogenated hydroxy compound, resulting in the liberation of hydrogen halide which is then allowed to escape.

The catalyst is preferably at least one compound selected from the group consisting of Mg, $MgCl_2$, $MgSO_4$, $MgCl(OH)$, $CaCl_2$, $ZnCl_2$, $(C_2H_5)_3NHCl$, $AlCl_3$, $(C_2H_5)_4NCl$, $TiCl_4$, $SnCl_4$ and $ZrCl_4$, more preferably $AlCl_3$, Mg, $MgCl_2$, and $MgSO_4$, and most preferably $AlCl_3$. Mixtures of two or more of these compounds are also possible. The amount of catalyst used in experiment ranged from about 0.01 moles/mole to about 0.20 moles/mole of phosphorus oxychloride, but variations as to this are possible. The higher loading amounts of Mg, $MgCl_2$ and $MgSO_4$ were required, along with overnight heating, to produce a conversion rate of about 90 percent, while AlCl$_3$ produced about the same yield using loading levels of only about 0.01 moles/mole and with only about two hours' heating.

The phosphorylation process involves making an admixture of the reactants, solvent and catalyst, heating the admixture to reflux temperature and refluxing it sufficiently to form a halogenated trialkyl phosphate ester precipitate. The order of mixing may be varied, although it is preferable that the catalyst be dissolved in the phosphorus oxyhalide and then this solution added to the solvent containing the halogenated hydroxy compound. Three requirements should ideally be met in choosing a solvent: (1) it should exhibit utility for dissolving the chosen halogenated hydroxy compound and phosphorus oxyhalide; (2) it should be substantially inert to the hydrogen halide that is evolved as a gas during the reaction; and (3) it should reflux preferably within the range of about 30° C. and about 200° C., and more preferably within the range of about 40° C. and about 150° C. This last recommendation is due to the fact that above this range decomposition is more likely to occur. Tetrachloroethylene, for example, is the most preferred solvent and refluxes at about 123° C. Other preferred solvents are tetrahydrofuran, methylene chloride, chloroform, a dioxane such as 1,4 dioxane (OCH$_2$CH$_2$OCH$_2$CH$_2$), carbon tetrachloride, ethylene dichloride, dimethyl sulfoxide, acetone and acetonitrile, and of these tetrahydrofuran, methylene chloride, and chloroform are more preferred.

The reflux process generally takes between about two and about four hours, although the timing can be varied to suit the reaction time and desired percent conversion. This process has excellent phosphorylation kinetics, and the final precipitate product is easily recovered. Where tribromoneopentyl alcohol, i.e., 3-bromo-2,2 bis(bromomethyl)propyl alcohol, is used as the halogenated hydroxy compound and phosphorus oxychloride as the phosphorus oxyhalide, the product is tris(tribromoneopentyl) phosphate, i.e., tris(3-bromo-2,2 bis(bromomethyl)propyl) phosphate, a compound which has good ultraviolet light stability and ignition resistance either by itself or as a component in ignition resistant compositions. Tris(tribromoneopentyl) phosphate usually precipitates as a high quality, snow white product by the method herein disclosed. Other possible precipitate products using phosphorus oxychloride include, for example, tris(trichloroneopentyl) phosphate when trichloroneopentyl alcohol is used as the halogenated hydroxy compound, and tris(chloro-dibromoneopentyl) phosphate when chloro-dibromoneopentyl alcohol is used as the halogenated hydroxy compound. The crystallization of the precipitate forms a slurry which may be washed a varying number of times, for example, with 1 N HCl or HBr, followed by washing with water a varying number of times. The wash amount may be geared to the solvent choice, with about 0.4 ml to about 0.8 ml of HCl or water used to about 1 ml of tetrachloroethylene, for example. Agitation helps to ensure maximization of product yield and is followed by phase separation. A compound such as sodium lauryl sulfate, sodium dodecyl sulfate or ammonium dodecyl sulfate, preferably sodium lauryl sulfate, may be added to facilitate phase sepration, and the precipitate may be recovered by various means, such as by filtration or other means of isolation. Drying by air, vacuum oven, etc., may be done to complete the process.

The following examples are illustrative of certain embodiments of the present invention and are not intended to be, nor should they be construed as being, limitative in any way. All parts and percentages are by weight unless otherwise indicated.

EXAMPLE 1

At room temperature, 252.57 g of 3-bromo-2,2 bis(bromomethyl)propyl alcohol, 1.07 g anhydrous aluminum chloride (particle size about 1 mm to about 50 mm) and 40.06 g phosphorus oxychloride were mixed in 804.2 g tetrachloroethylene in a 1,000 ml three-neck round-bottom flask. The flask was equipped with a water-cooled condenser, a mechanical stirrer and a dropping funnel, and was heated using an electric muffle. The contents of the flask were heated over 9 minutes to refluxing at about 123° C. Refluxing was continued for 1 hour and 55 minutes, after which the contents were cooled to room temperature. A white precipitate formed and was filtered and then dried at 100° C. in a vacuum oven at 28–29" vacuum. This precipitate weighed 234 g after drying. It was assayed by a liquid chromatographic method and shown to be tris (3-bromo-2,2 bis(bromomethyl)propyl) phosphate. The m.p. was about 175° C. to about 178° C. This isolated yield represented 89 percent of calculated yield based on the starting amount of the tribromoneopentyl alcohol.

EXAMPLE 2

In an 8,000 ml reactor 2,445 g of 3-bromo-2,2 bis(bromomethyl)propyl alcohol was dissolved in 4,000 ml tetrachloroethylene. The reactor was equipped with a water-cooled condenser connected to a caustic scrubber, a 500 ml dropping funnel and a mechanical agitator. The reactor jacket was heated by circulating oil from a constant temperature bath.

In a separate flask 10.37 g anhydrous aluminum chloride (particle size about 1 mm to about 50 mm) was dissolved in 400 g phosphorus oxychloride. While heating the reactor flask containing the tetrachloroethylene solution to reflux, the phosphorus oxychloride solution was gradually added through the dropping funnel. Refluxing was continued for 2 hours and 30 minutes, during which time the reaction was monitored by a liquid chromatographic method. At the end of this reflux time the reaction was substantially complete. The solution was then cooled to 70° C. and a white precipitate formed. The slurry was washed 3 times with 2,500 ml of a 5 percent aqueous HCl solution, at room temperature, in order to remove the aluminum chloride catalyst. The slurry was finally cooled to room temperature and the solid filtered by means of suction filtration and dried at 100° C. in a vacuum oven at 28–29" vacuum. The yield was 2,349 g of white tris(3-bromo-2,2 bis(bromomethyl)propyl) phosphate, a 92 percent yield based on the starting amount of the tribromoneopentyl alcohol. The melting point was found to be 175° C. to 178° C.

EXAMPLE 3

Following the procedures outlined in Example 2, 150 g of 3-bromo-2,2 bis(bromomethyl)propyl alcohol, 0.57 g titanium tetrachloride and 25 g phosphorus oxychloride were mixed in 300 ml of tetrachloroethylene in a flask. The contents were heated at refluxing for 5 hours and 30 minutes. Cooling, washing, filtering and drying steps were the same as in the previous example. The product was 140 g of tris(3-bromo-2,2 bis(bromomethyl)propyl) phosphate, or an 89 percent yield based on the tribromoneopentyl alcohol.

EXAMPLE 4

Following the procedures outlined in Example 1, 150 g of 3-bromo-2,2 bis(bromomethyl)propyl alcohol, 3 g anhydrous magnesium chloride and 25 g phosphorus oxychloride were mixed in 300 ml tetrachloroethylene in a flask. The contents were heated at reflux temperature for 21 hours. Following the described cooling, filtering and drying, a dry white product of 130 g of tris(3-bromo-2,2 bis(bromomethyl)propyl) phosphate was obtained, making an 83 percent yield based on the tribromoneopentyl alcohol.

EXAMPLE 5

Following the procedures described in Example 1, 150 g of 3-bromo-2,2 bis(bromomethyl)propyl alcohol, 2 g anhydrous aluminum chloride and 33 g phosphorus oxychloride were mixed in 300 ml ethylene dichloride in a flask. The contents were heated at refluxing (88° C.) for 4 hours. Liquid chromatographical monitoring revealed excess phosphorus oxychloride, of about 40 percent at this point, and an additional 55 g of the alcohol was added. The contents were heated for an additional 19 hours and 30 minutes. Following cooling, filtering and drying, 184 g of white tris(3-bromo-2,2 bis(bromomethyl)propyl) phosphate was obtained, i.e., an 86 percent yield based on the tribromoneopentyl alcohol.

EXAMPLE 6

Using the procedure in Example 1, 150 g of 3-bromo-2,2 bis(bromomethyl)propyl alcohol, 4.77 g of anhydrous aluminum chloride (particle size about 1 mm to about 50 mm) and 25 g of phosphorus oxychloride were mixed in 400 ml chloroform in a flask. The contents were heated at reflux temperature (63° C. to 64° C.) and the reaction monitored using a liquid chromatographic method. When monitoring showed an excess of the alcohol, an additional 1.8 g of phosphorus oxychloride was added. After a total reflux time of 20 hours and 20 minutes, and cooling, filtering and drying as described, 122 g of white tris(3-bromo-2,2 bis(bromomethyl)propyl) phosphate, a 78 percent yield, was obtained based on the tribromoneopentyl alcohol.

EXAMPLE 7

Into 300 ml of methylene choride in a flask were mixed 150 g of 3-bromo-2,2 bis(bromomethyl)propyl alcohol, 5.1 g anhydrous aluminum chloride (particle size about 1 mm to about 50 mm), and 25 g phosphorus oxychloride. The solution was heated at refluxing for 4 hours and 25 minutes, and an additional 3 g of the anhydrous aluminum chloride was added. The contents were continued heating at the same temperature for 18 hours and 20 minutes. During cooling to room temperature, a white precipitate formed. The slurry was washed twice with 500 ml of an aqueous 5 percent HCl solution followed by one washing with 500 ml of water. After drying at 100° C. in a vacuum oven at 28–29" vacuum, the white product was determined to be 150 g of tris(3-bromo-2,2 bis(bromomethyl)propyl) phosphate, which is a 95 percent yield based on the tribromoneopentyl alcohol.

We claim:
1. A method of producing a halogenated trialkyl phosphate ester which comprises:
admixing a haloneopentyl alcohol containing a halogen selected from the group consisting of Br, Cl, I and mixtures thereof, a phosphorus oxyhalide containing a halogen selected from the group consisting of Br, Cl, I and mixtures thereof, a solvent suitable to dissolve said haloneopentyl alcohol and said phosphorus oxyhalide, said solvent being substantially inert to hydrogen halide, and a catalyst suitable to increase the polarity of said phosphorus oxyhalide;
refluxing said admixture sufficiently to form a halogenated trialkyl phosphate ester precipitate; and
recovering said precipitate.
2. The method of claim 1 wherein the halogen is Br.
3. The method of claim 1 wherein the halogen is Cl.
4. The method of claim 1 wherein the halogen is I.
5. The method of claim 1 wherein the halogen is a mixture of at least two elements of the group consisting of Br, Cl and I.
6. The method of claim 1 wherein said haloneopentyl alcohol is chloro-dibromo-neopentyl alcohol.
7. The method of claim 1 wherein said haloneopentyl alcohol is bromo-dichloroneopentyl alcohol.
8. The method of claim 1 wherein said solvent is tetrachloroethylene.
9. The method of claim 1 wherein said solvent is tetrahydrofuran.
10. The method of claim 1 wherein said solvent is methylene chloride.
11. The method of claim 1 wherein said solvent is chloroform.
12. The method of claim 1 wherein said solvent is a dioxane.
13. The method of claim 1 wherein said solvent is carbon tetrachloride.
14. The method of claim 1 wherein said solvent is dimethyl sulfoxide.
15. The method of claim 1 wherein said solvent is acetonitrile.
16. The method of claim 1 wherein said solvent is ethylene dichloride.
17. The method of claim 1 wherein said catalyst is $AlCl_3$.
18. The method of claim 1 wherein said catalyst is Mg.
19. The method of claim 1 wherein said catalyst is MgCl(OH).
20. The method of claim 1 wherein said catalyst is $(C_2H_5)_3$ NHCl.
21. The method of claim 1 wherein said catalyst is $MgCl_2$.
22. The method of claim 1 wherein said catalyst is $MgSO_4$.
23. The method of claim 1 wherein said catalyst is $(C_2H_5)_4$ NCl.
24. The method of claim 1 wherein said catalyst is $TiCl_4$.
25. The method of claim 1 wherein said catalyst is $SnCl_4$.
26. The method of claim 1 wherein said catalyst is $ZrCl_4$.
27. The method of claim 1 wherein said haloneopented alcohol is admixed with said phosphorus oxyhalide in a mole ratio within the range of about ten to one and about one to one.

28. The method of claim 1 wherein said haloneopented alcohol is admixed with said phosphorus oxyhalide in a mole ratio within the range of about four to one and about two to one.

29. The method of claim 1 wherein said haloneopented alcohol is admixed with said phosphorus oxyhalide in a mole ratio of about three to about one.

30. The method of claim 1 wherein said refluxing is carried out within the range of about 30° C. and about 200° C.

31. The method of claim 1 wherein said refluxing is carried out within the range of about 40° C. and about 150° C.

32. The method of claim 1 wherein said recovery is by filtration.

33. A method of producing tris(tribromoneopentyl) phosphate which comprises:
   admixing tribromoneopentyl alcohol, phosphorus oxychloride, tetrachloroethylene and aluminum chloride;
   refluxing said admixture sufficiently to form a tris(tribromoneopentyl) phosphate precipitate; and
   recovering said precipitate.

34. The method of claim 33 wherein said tribromoneopentyl alchol is admixed with said phosphorus oxychloride in a mole ratio within the range of about ten to about one and about one to about one.

35. The method of claim 33 wherein said tribromoneopentyl alcohol is admixed with said phosphorus oxychloride in a mole ratio within the range of about four to about one and about two to about one.

36. The method of claim 33 wherein said tribromoneopentyl alcohol is admixed with said phosphorus oxychloride in a mole ratio of about three to about one.

37. A method of producing a halogenated trialkyl phosphate ester which comprises:
   admixing a haloneopentyl alcohol containing a halogen selected from the group consisting of Br, Cl, I and mixtures thereof, a solvent suitable to dissolve the haloneopentyl alcohol and the phosphorus oxyhalide, said solvent being substantially inert to hydrogen halide, and a catalyst selected from the group consisting of Mg, $MgCl_2$, $MgSO_4$, MgCl(OH), $(C_2H_5)_3NHCl$, $AlCl_3$, $(C_2H_5)_4NCl$, $TiCl_4$, $SnCl_4$ and $ZrCl_4$;
   refluxing said admixtures sufficiently to form a halogentated trialkyl phosphate ester precipitate; and
   recovering said precipitate.

38. The method of claim 37 wherein the halogen is Br.

39. The method of claim 37 wherein the halogen is Cl.

40. The method of claim 37 wherein the halogen is I.

41. The method of claim 37 wherein the halogen is a mixture of at least two elements of the group consisting of Br, Cl and I.

42. The method of claim 37 wherein said halogenated hydroxy compound is chloro-dibromo-neopentyl alcohol.

43. The method of claim 37 wherein said halogenated hydroxy compound is bromo-dichloroneopentyl alcohol.

44. The method of claim 37 wherein said solvent is tetrachloroethylene.

45. The method of claim 37 wherein said solvent is tetrahydrofuran.

46. The method of claim 37 wherein said solvent is methylene chloride.

47. The method of claim 37 wherein said solvent is choloroform.

48. The method of claim 37 whrein said solvent is a dioxane.

49. The method of claim 37 wherein said solvent is carbon tetrachloride.

50. The method of claim 37 wherein said solvent is dimethyl sulfoxide.

51. The method of claim 37 wherein said solvent is acetonitrile.

52. The method of claim 37 wherein said solvent is ethylene dichloride.

53. The method of claim 37 wherein said halogenated hydroxy compound is admixed with said phosphorus oxyhalide in a mole ration within the range of about ten to one and about one to one.

54. The method of claim 37 wherein said halogenated hydroxy compound is admixed with said phosphorus oxyhalide in a mole ratio within the range of about four to one and about two to one.

55. The method of claim 37 wherein said halogenated hydroxy compound is admixed with said phosphorus oxyhalide in a mole ratio of about three to about one.

56. The method of claim 37 wherein said refluxing is carried out within the range of about 30° C. and about 200° C.

57. The method of claim 37 wherein said refluxing is carried out within the range of about 40° C. and about 150° C.

58. The method of claim 37 wherein said recovery is by filtration.

* * * * *

UNITED STATES PATENT AND TRADEMARK OFFICE
CERTIFICATE OF CORRECTION

PATENT NO. : 4,714,771

DATED : December 22, 1987

INVENTOR(S) : Ming-Biann Lu

It is certified that error appears in the above-identified patent and that said Letters Patent is hereby corrected as shown below:

Cover page, in the second line under "Other Publications" "Transtation" should read -- Translation -- .

Col. 2, line 61, "$SnCl_4$and" should read -- $SnCl_4$ and -- .

Col. 3, line 68, "sepration" should read -- separation -- .

Col. 6, lines 65-66 (Claim 27), "haloneopented" should read -- haloneopentyl --.

Col. 7, lines 1-2 (Claim 28), "haloneopented" should read -- haloneopentyl -- ;

lines 5-6 (Claim 29), "haloneopented" should read -- haloneopentyl -- ;

line 26 (Claim 34), "alchol" should read -- alcohol -- ;

line 41 (Claim 37), between "thereof," and "a" insert -- a phosphorus oxyhalide containing a halogen selected from the group consisting of Br, Cl, I and mixtures thereof, -- .

Col. 8, lines 8-9 (Claim 42), "halogenated hydroxy compound" should read -- haloneopentyl alcohol -- ;

lines 11-12 (Claim 43), "halogenated hydroxy compound" should read -- haloneopentyl alcohol -- ;

lines 32-33 (Claim 53), "halogenated hydroxy compound" should read -- haloneopentyl alcohol -- .

UNITED STATES PATENT AND TRADEMARK OFFICE
CERTIFICATE OF CORRECTION

PATENT NO. : 4,714,771

DATED : December 22, 1987

INVENTOR(S) : Ming-Biann Lu

It is certified that error appears in the above-identified patent and that said Letters Patent is hereby corrected as shown below:

Col. 8, lines 36-37 (Claim 54), "halogenated hydroxy compound" should read -- haloneopentyl alcohol -- ;

lines 40-41 (Claim 55), "halogenated hydroxy compound" should read -- haloneopentyl alcohol -- .

Signed and Sealed this

Twentieth Day of September, 1988

Attest:

DONALD J. QUIGG

*Attesting Officer*  *Commissioner of Patents and Trademarks*